United States Patent [19]

Herweh

[11] Patent Number: 4,650,846

[45] Date of Patent: Mar. 17, 1987

[54] NOVEL POLYACRYLIC ESTERS BEARING PENDANT MACROCYCLIC ETHERS AND ELECTRICALLY CONDUCTING COMPOSITIONS COMPRISED THEREOF

[75] Inventor: John E. Herweh, East Hempfield Township, Lancaster County, Pa.

[73] Assignee: Armstrong World Industries, Inc., Lancaster, Pa.

[21] Appl. No.: 835,290

[22] Filed: Mar. 3, 1986

Related U.S. Application Data

[62] Division of Ser. No. 710,448, Mar. 11, 1985, Pat. No. 4,607,110.

[51] Int. Cl.$^4$ .............................................. C08F 20/30
[52] U.S. Cl. ................................................... 526/268
[58] Field of Search ................................. 526/266, 268

[56] References Cited

U.S. PATENT DOCUMENTS

| 3,090,790 | 5/1963 | Braun | 526/266 |
| 3,687,978 | 8/1972 | Pedersen | 526/266 |

Primary Examiner—Paul R. Michl
Attorney, Agent, or Firm—Russell, Georges & Breneman

[57] ABSTRACT

The present invention relates to polyacrylic ester polymers having pendant macrocyclic ethers as well as electrically-conducting compositions comprised thereof.

6 Claims, No Drawings

NOVEL POLYACRYLIC ESTERS BEARING PENDANT MACROCYCLIC ETHERS AND ELECTRICALLY CONDUCTING COMPOSITIONS COMPRISED THEREOF

CROSS REFERENCE TO RELATED APPLICATIONS

This application is a division of application, Ser. No. 710,448, filed Mar. 11, 1985 and issued as U.S. Pat. No. 4,607,110 on Aug. 19, 1986.

BACKGROUND OF THE PRESENT INVENTION

The present invention relates to polyacrylic ester polymers bearing pendant macrocyclic ethers.

Substantial interest in macrocyclic ethers has developed since their invention was reported by C. J. Pedersen in the late 1960's. Many of these ethers, and in particular those comprising the 18-crown-6 moiety, have proved quite useful in the complexing of alkali metal, alkaline earth and other cations.

A number of U.S. patents have issued to C. J. Pedersen and co-workers relating to the preparation and use of various crown ethers including U.S. Pat. Nos. 3,361,778; 3,562,295; 3,686,225; 3,687,978; 3,856,813; and 3,873,569.

Although certain interest has been shown in developing polymeric materials which comprise crown ethers, the uses for these materials have tended to parallel those of the non-polymerized crown ethers, and little emphasis has been placed on the uniqueness which is attributable to a polymer matrix.

Generally, two types of polymers have been produced comprising crown ethers, specifically (1) polymers in which the crown ether moiety is pendant from the polymer backbone; and (2) polymers in which the crown ether moiety is incorporated into the polymer backbone.

With regard to the former, various disclosures exist regarding the complexing behavior of addition polymers bearing macroheterocyclic structures as pendant groups including Jaycox, Gary D. et al, *J. Polymer Sci,* 20, 1629 (1982) and *Proceedings IUPAC Macromolecular Symposium,* U. of Mass., Amherst, Mass., July 12–16, 1982, p. 99.

An example of the latter relates to work wherein a dibenzo-18-crown-6 was nitrated in both benzene rings and the nitro groups were reduced. The resulting isomeric diamines were then interacted with diacid chlorides to provide polyamides. Commonly-assigned U.S. Pat. No. 4,438,251 (issued to Herweh) is directed to polyurethane polymers comprising macrocyclic crown ethers in the polymer backbone. Reference is also made to the incorporation of macroheterocyclic structures into a polymer chain in Mathis, L. et al, *J. Polymer Sci.* A18, 2911 (1980); Gramain, P. et al, *Ind. Eng. Chem. Prod. Res. Dev.,* 20, 524 (1981); and Herweh, J. et al, *J. Polymer Sci.,* 21, 3101 (1983).

Concurrent with the noted interests has been the attention afforded the development of polymers possessing, in addition to the strength, elasticity, plasticity and toughness typically associated with metals, the property of electrical conductance. The importance of this objective lies in the significance of being able to process such material in the form of films, foils, fibers, etc. in accordance with established procedures.

OBJECTS AND SUMMARY OF THE INVENTION

It is accordingly one object of the present invention to provide novel polymers comprising pendant crown ethers.

It is accordingly another object of the present invention to provide polymeric substrates comprised of polymers having pendant crown ethers, the polymers being useful for a variety of purposes.

It is accordingly another object of the present invention to provide polymeric substrates comprised of polymers having pendant crown ethers which substrates are useful in the complexing of alkaline earth, alkali metal and other cations.

It is yet another object of the present invention to provide polymeric substrates comprised of polymers having pendant crown ethers which, when complexed with cation materials or neutral electron acceptor molecules, serve as electrically conductive materials.

In its broadest aspect the present invention relates to a polymerizable monomer having the formula:

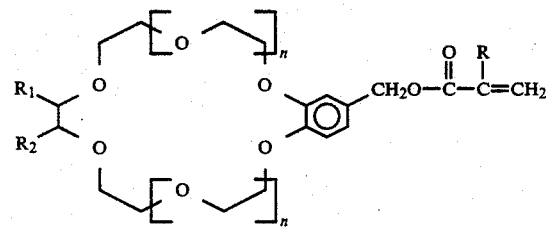

wherein $n = 1-3$, R is hydrogen or methyl, $R_1$ and $R_2$ are hydrogen or in combination with the macrocyclic ether ring form a phenyl ring and wherein at least some of the hydrogen atoms present upon the aromatic rings optionally may be replaced by an alkyl group of 1 to 4 carbon atoms.

Accordingly, the phenyl ring bearing the acrylic ester and the phenyl ring formed by $R_1$ and $R_2$ may be substituted or unsubstituted. The substituents on each or either aromatic ring suitably are lower alkyl groups of 1 to 4 carbon atoms.

In accordance with another aspect of the present invention, there is provided a polymerizable monomer having the formula:

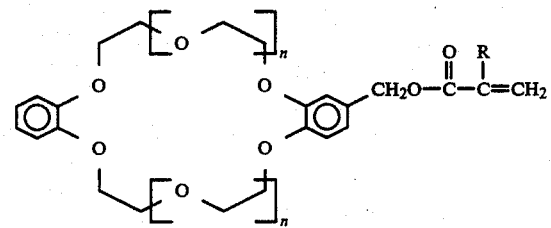

wherein $n = 1-3$, R is selected from the group consisting of hydrogen or methyl and wherein at least some of the hydrogen atoms present upon the aromatic rings optionally may be replaced by an alkyl group of 1 to 4 carbon atoms.

In accordance with another aspect of the present invention, there is provided a polyacrylic ester polymer comprised of a moiety having the formula:

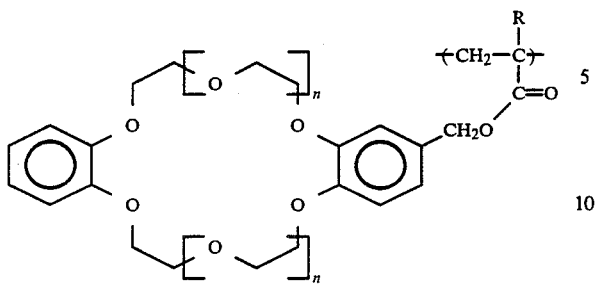

wherein n=1–3, R is selected from the group consisting of hydrogen and methyl and wherein at least some of the hydrogen atoms present upon the aromatic rings optionally may be replaced by an alkyl group of 1 to 4 carbon atoms.

Yet another aspect the present invention relates to a polyacrylic ester polymer comprised of a moiety having the formula:

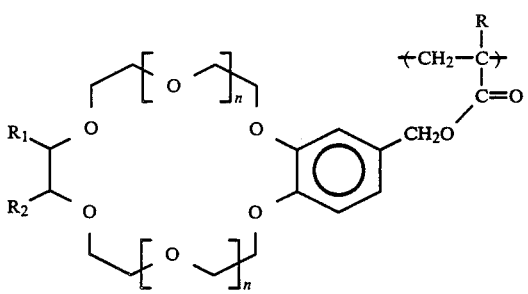

wherein n=1–3, R is hydrogen or methyl, $R_1$ and $R_2$ are hydrogen or in combination with the macrocyclic ether ring form a phenyl ring and wherein at least some of the hydrogen atoms present upon the aromatic rings optionally may be replaced by an alkyl group of 1 to 4 carbon atoms.

Accordingly, the phenyl ring bearing the acrylic ester and the phenyl ring formed by $R_1$ and $R_2$ may be substituted or unsubstituted. The substituents on each or either aromatic ring suitably are lower alkyl groups of 1 to 4 carbon atoms.

In accordance with yet another aspect of the present invention there are provided electrically-conductive compositions comprised of a complex of a metallic salt and a polyacrylic ester polymer comprised of a moiety having the above-identified formulae.

DETAILED DESCRIPTION OF THE INVENTION

The polyether ring system used to practice the present invention preferably comprises a mono-or diphenylene-18-crown-6 moiety.

The preferred diphenylene and phenylene-18-crown moieties are identified by the following formulae:

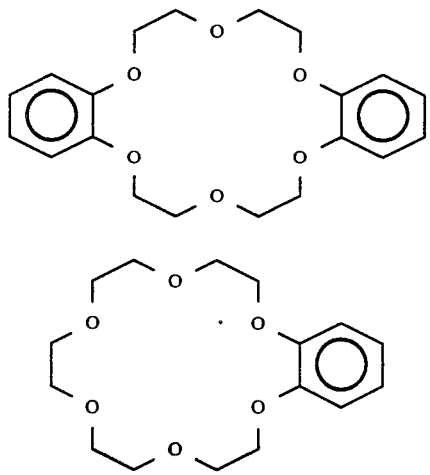

The polyether alcohols comprising these moieties may be prepared by means which are well known in the art. For example, in the case of the dibenzo bearing ring system, 3,4-dihydroxybenzaldehyde (a substituted catechol) may be interacted with 1,2-bis[2'-(2''-chloroethoxy)ethoxy]benzene according to general literature procedures to provide 2,3-(4'-formyl benzo)-11,12-benzo-18-crown-6 product. Similarly, if 1,2-bis(2'-chloroethoxy)benzene or 1,2-bis[2'-(2''-chloroethoxy)diethoxy]benzene are substituted for 1,2-bis(2'-(2''-chloroethoxy)ethoxy]benzene, the 12-crown-4 or 24-crown-8 moiety, respectively, can be obtained. The formyl function can then be reduced to the alcohol form.

In the case of the monobenzo bearing ring system the 3,4-dihydroxybenzaldehyde may be interacted with 1,14-dichlorotetraoxatetradecane according to general literature procedures to provide 2,3-(4'-formylbenzo)-18-crown-6. Similarly if 1,8-dichlorodioxaoctane or 1,20-dichlorohexaocaeicosane are substituted for 1,14-dichlorotetraoxatetradecane the 12-crown-4 or 24-crown-8 moiety, respectively, can be obtained.

Hydroxylated ring substituents must be prepared for use according to the present invention in order to ultimately form the acrylic ester monomer. These materials are derivable from aldehydes which are commercially available, or which are prepared according to literature methods. Primary alcohols may be prepared by reacting catechol aldehydes of the formula

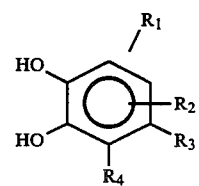

where $R_1$ is —$COR_5$, $R_2$, $R_3$, and $R_4$ are independently H or $CH_3$, and $R_5$ is H, and then reducing the aldehyde to the alcohol after interaction of the catechol to form the crown ether. The various alcohols may then be prepared by reduction using, for example, sodium borohydride.

With regard to the acrylic portion of the polymers of the present invention, acrylic acid-derived (i.e., where R is hydrogen) and methacrylic acid-derived moieties may be employed. For example, methacryloyl chloride may be reacted with the alcohol substituent discussed above to provide the desired methacrylate monomer.

The polyacrylic ester polymers of the present invention have been found to exhibit highly effective cation-binding ability, especially in contrast to the dibenzo-18-crown-6 ether as well as to polymers wherein the crown ether structure comprises part of the polymer backbone (e.g., a polyurethane as disclosed in commonly-assigned U.S. Pat. No. 4,438,251).

The procedure described by Pedersen, C. J. et al in *Fed. Proc., Fed. Amer. Soc. Exp. Biol.* 1968, 27, 1305 was employed to determine the extent of the formation of complexes between various crown ethers and alkali metal salts. The determination was made by means of solvent extraction and UV spectral determination of the extracted picrate ion. Methylene chloride was used as the organic phase with crown ether, and the concentration of the alkali and alkaline earth metal hydroxides was 0.01M. The concentration of the crown ether was $7 \times 10^{-4}$M in all instances except for $K^+$ (molar ratios of ½ and 1/20), $Na^+$ (molar ratio of ½) and $Ba^{++}$ (molar ratio of 1/20) where the concentration was $1.4 \times 10^{-3}$M. The concentration of the picrate was $7 \times 10^{-4}$M except for $K^+$ (molar ratios of 1/10 and 1/20) where the concentration was $7 \times 10^{-5}$M. The results of the noted comparisons are set forth in Table I below, with the results for crown ethers A and B having been previously-reported by Herweh, J. E. et al, *J. Polym. Sci.*, 21, 3101 (1983):

TABLE I

Ion-Binding Capability of Various Crown Ethers
Extraction % Based on Picric Acid

| Crown Ether | Mol Ratio Pi/CE $K^+$ | | | | Pi/CE $Na^+$ Mol Ratio | | Pi/CE $Ba^{++}$ Mol Ratio | |
|---|---|---|---|---|---|---|---|---|
| | 1/1 | 1/2 | 1/10 | 1/20 | 1/1 | 1/2 | 1/10 | 1/20 |
| A | 26.4 | 31.5 | 34.4 | 50.1 | 1.3 | 1.2 | 2.6 | 3.6 |
| B | 20.5 | 26.0 | 28.3 | 49.0 | 7.1 | — | 2.9 | 4.8 |
| C | 32.1 | 39.8 | 52.1 | 72.3 | 6.0 | 8.8 | 8.1 | 12.1 |

A = Dibenzo-18-crown-6
B = Polyurethane having crown ether A within chain
C = Polymethacrylic ester bearing pendant crown ether A The extractive efficiencies of the various crown ethers identified in Table I indicates that the polyacrylic ester polymer C of the present invention exhibits an overall extractive efficiency greater than the efficiency exhibited by the other types of crown ethers (denoted as A and B). The particularly noteworthy complexing of $K^+$ may be due to the formation of sandwich type 1:2 complexes betweeen the metal cation and two adjacent crown ether moieties which are present as pendant groups along the polymer chain.

The ion-binding ability of the polymethacrylic ester bearing crown ether structures was applied to several metal-7,7,8,8-tetracyanoquinodimethane (TCNQ) salts that are virtually insoluble in water and in organic solvents. The complexation of metal-TCNQ salts with various nonpolymeric macroheterocyclics has been reported. Japanese patent 80-45,641 (CA 93 18645r (1980) describes the formation of dibenzo-18-crown-6 complexes with alkali metal-TCNQ salts. Such complexes reportedly have high electrical conductivities and solubility in organic solvents.

When a solution of 1,2-dichloroethane and the polymethacrylic ester of the present invention bearing crown ether structures was agitated with $K^+$ TCNQ.$^-$, a deep green color rapidly developed in the organic phase. In a specific case where the crown ether bearing polymethacrylic ester polymer ($1 \times 10^{-2}$M in 1,2-dichloroethane) was contacted with $6 \times 10^{-5}$ mol of $K^+$TCNQ.$^-$ and the visible spectrum recorded after 1 hour, a spectrum was obtained that was consistent in the 400–750 nm region with that reported by Hertler et al, *J. Amer. Chem Soc.*, 84, 3374 (1962) for the TCNQ radical anion. Solid complexes, typically an intense iridescent green to an iridescent blue-green in color, were obtained by stirring a solution of the polymer of the present invention in 1,2-dichloroethane with an excess of the metal-TCNQ salt (typically at 1:2 molar ratio of polymer to metal-TCNQ salt). The soluble complexes were isolated from the solvent phase by removal of volatiles in vacuo. Conductivity determinations, carried out using the three-probe method in a powder compaction cell, gave values that in the case of $K^+$ and $Cs^+$ were several orders of magnitude lower than that of the corresponding metal-TCNQ.$^-$ salt alone as noted in Table II. In the case of the $Cu^{+2}$ (TCNQ.$^-$)$_2$ salt, the conductivity of the crown ether bearing polymer solubilized metal-TCNQ salt and the metal-TCNQ salt alone were comparable as also noted in Table II below:

TABLE II

Electrical Properties of Metal-TCNQ Salts Solubilized via Complexation with a Polymethacrylate Bearing Pendant Crown Ether Structures

| $M^{+n}$ (TCNQ.$^-$) | Conductivity S/cm | Crown Ether (CE) Solubilized $M^{+n}$ (TCNQ.$^-$) | Conductivity S/cm |
|---|---|---|---|
| $K^+$ TCNQ.$^-$ | $2 \times 10^{-4}$ | CE ($K^+$ TCNQ.$^-$) | $2 \times 10^{-8}$ |
| $Cs_2^+$ (TCNQ.$^-$)$_2$ TCNQ | $1 \times 10^{-5}$ | CE[$Cs_2^+$ (TCNQ.$^-$)$_2$TCNQ] | $5 \times 10^{-7}$ |
| $Cu^{+2}$ (TCNQ.$^-$)$_2$ | $5 \times 10^{-3}$ | CE[$Cu^{+2}$ (TCNQ.$^-$)$_2$] | $5 \times 10^{-3}$ |

The invention is additionally illustrated in connection with the following Examples which are to be considered as illustrative of the present invention. It should be understood, however, that the invention is not limited to the specific details of the Examples.

EXAMPLE I

Preparation of 4-formyldibenzo-18-crown-6 ether

A solution of 3,4-dihydroxybenzaldehyde (27.3 g, 0.197 mol) in 500 ml of n-butanol was sparged for 0.5 hour with $N_2$. Sodium hydroxide (15.8 g, 0.395 mol) was quickly added and the mixture was heated to reflux. To the refluxing solution 63.8 g (0.197 mol) of 1,2-bis[2'-(2''-chloroethoxy)ethoxy]benzene was added with stirring over a period of 75 minutes. Upon completing the addition, the reaction mixture was heated at reflux for 3 hours and then cooled to 50°–60° C. and acidified with 2.5N HCl. The acidulated reaction mixture was heated to reflux and ca. 130 ml of butanol was distilled. Water was added dropwise while the distillation was continued—the rates of addition and distillate formation being of similar magnitude.

After ca. 400 ml of distilate had been removed, acetone (200 ml) was added and the finely divided tan solid filtered and dried in vacuo in the presence of P₂O₅. The dried reaction product, 31.5 g was triturated with boiling benzene and gave 24.1 g (0.062 mol) of 4-formyl-dibenzo-18-crown-6, mp 192°–5° C.; ¹H-NMR (CDCl₃) 4.0 (m, —OCH₂CH₂O—), 6.8–7.5 (m, aryl protons), and 9.8 ppm (s, —CHO) of the formula:

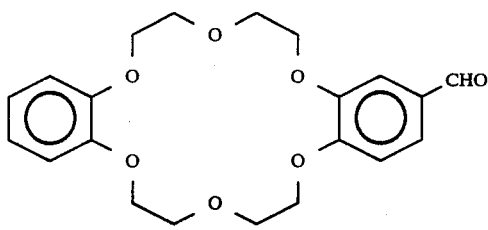

Preparation of 4-methyloldibenzo-18-crown-6 ether

Sodium borohydride (1.99 g, 0.053 mol) was rapidly added to a stirred slurry of 4-formyl-dibenzo-18-crown-6 (10.2 g, 0.026 mol) in 200 ml of dry glyme. The resulting mixture was left to stir at room temperature for several days. The reaction mixture was quenched by its addition to 175 ml of water. Dilute acetic acid was subsequently added with cooling to the resulting weakly basic reaction mixture until it was neutral. The mixture was filtered to remove small amounts of insoluble matter and the filtrate was concentrated to ¼ its original volume on a Rota-vap at reduced pressure. The concentrate was cooled and the precipitated solid filtered, washed with cold water and dried in vacuo to yield 8.91 g (88%) of 4-methyloldibenzo-1-8-crown-6 ether, m.p. 168°–172° C. of the formula:

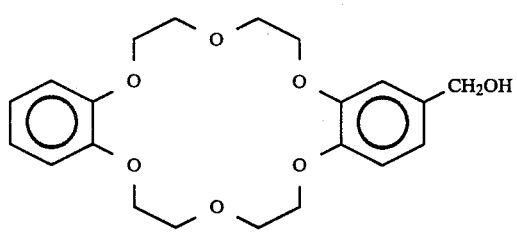

Preparation of 4-methyloldibenzo-18-crown-6 methacrylate 4-methyloldibenzo-18-crown-6 (12.8 g, 33 mmol) and 128 ml of dry dimethylformamide were quickly added to a flame dried reactor and the mixture warmed to ca. 50° C. to dissolve the 4-methyloldibenzo-18-crown-6. Dry benzene (65 ml) and triethyl amine (6.7 g, 66 mmol) was added and the stirred solution was cooled to 25° C. under a nitrogen atmosphere.

A solution of freshly distilled methacryloyl chloride (4.1 g, 39 mmol) in 10 ml of dry benzene was added in 5 minutes with stirring and cooling in ice water. After 24 hours at room temperature the reaction mixture was filtered; the filter-cake washed with ether and dried in vacuo was identified as triethyl amine hydrochloride (4.3 g, 95% of theoretical). The clear pale yellow filtrate was flash distilled at 0.3 mm (still temperature <90° C.) and left a pale tan solid residue. The solid residue was triturated with water and filtered. The water insoluble filter-cake was dissolved in methylene dichloride (200 ml) and the resulting solution dried over molecular sieves. Concentration of the dry methylene dichloride solution gave 12.5 g of crude 4-methylol-dibenzo-18-crown-6-methacrylate (83%). The crude product was chromatographed over alumina using chloroform/methanol (99:1) as the eluant. Analytically pure 4-methyloldibenzo-18-crown-6 methacrylate (8.5 g, 56%), mp 145°–8° C. was recovered of the formula:

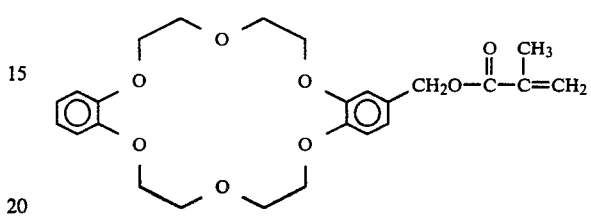

Polymerization of 4-methyloldibenzo-18-crown-6 methacrylate 4-methyloldibenzo-18-crown-6 (7.8 g, 17 mol) was added to 100 ml of dry benzene and the stirred solution was heated to reflux. A solution of 2,2′-azobis[isobutyronitrile] (0.015 g, 0.5 mol %) in ca. 2 ml of dry benzene was added and refluxing continued. After ca. 3 hours, a second addition of 2,2′azobis[isobutyronitrile] was made and reflux temperatures were maintained for 16 hours. Thin layer chromatography (alumina, CHCl₃/CH₃OH-99/1) indicated that most of the following monomer had disappeared (polymerized):

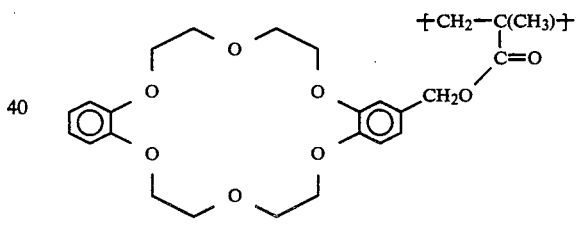

After concentration to remove solvent a viscous gum remained. This residue was dissolved in methylenee dichloride and the resulting clear pale yellow solution added to 600 ml of ice-cold hexane. The white solid precipitate was filtered with suction and the filter-cake washed with fresh hexane and dried in vacuo at 60° C. The dried polymer 7.65 g (98% ) had a Tg of 67° C. (by DSC, mid-range on reheat). Anal. Calcd. for C₂₅H₃₀O₈: C, 65.49; H, 6.60. Found: C, 65.46 and 65.27; H, 6.74 and 6.79. The high and low values for the molecular weight distribution of the polymer were about 49,000 and 4,900 respectively.

EXAMPLE II

Preparation of 4-formylbenzo-18-crown-6 ether

A solution of 3,4-dihydroxybenzaldehyde (19 g, 0.138 mol) in 400 ml of n-butanol was given a sub-surface sparge with helium for 0.5 hr. The clear rust colored solution was treated with 11.7 g (0.293 mol) of sodium hydroxide in 30 ml of water. The reaction mixture developed an amber color and was heated to gentle reflux while maintaining a helium atmosphere. To the stirred gently refluxing solution was added 37.4 g (0.136 mol) of 1,14-dichloro tetraoxatetradecane.

Upon completing the addition, the amber colored reaction mixture was maintained at reflux for 24 hours. The reaction mixture was cooled to room temperature and acidified with 18% hydrochloric acid while cooling in an ice bath. A crystalline solid precipitated and was filtered with suction. The filter-cake was largely water soluble and was discarded as sodium chloride. The filtrate, upon distillation at reduced pressure, left a dark brown residual oil. The residual oil was extracted with hot hexane. Concentration of the combined hexane extracts left an oily solid identified as 4-formylbenzo-18-crown-6 (b 11.2 g, 0.033 mol); 'H-NMR(CDCl$_3$) 3.6 (m, —(OCH$_2$CH$_2$O)$_3$—, 3.9 (m, ArOCH$_2$CH$_2$O—), 4.2 (m, ArOCH$_2$CH$_2$O—), 7.2 (complex m, aryl) and 9.8 ppm (s, —CHO) of the formula:

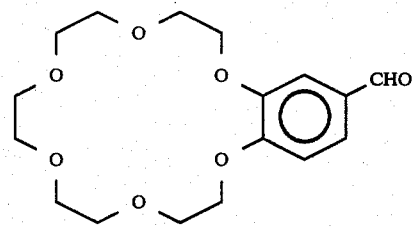

Preparation of 4-methylolbenzo-18-crown-6 ether

Sodium borohydride (0.42 g, 0.011 mol) was added to a solution of 4-formylbenzo-18-crown-6 (3.7 g, 0.011 mol) in 75 ml of dry glyme. The resulting solution was left to stir at room temperature for 68 hours, and it was then added to 100 ml of water and neutralized with concentrated acetic acid. The neutralized solution was concentrated on a Rota-vap at reduced pressure. The liquid concentrate was then extracted with chloroform and the combined extracts dried over magnesium sulfate. Distillation of the dried chloroform solution left an oil identified as 4-methylolbenzo-18-crown-6, 1.85 g (0.005 mol); 'H—NMR(CDCl$_3$) 3.69 (d, —OCH$_2$C-H$_2$O)$_3$), 2.8 (s, OH), 3.9 (m, ArOCH$_2$CH$_2$O—), 4.1 (m, ArOCH$_2$CH$_2$O—), 4.6 (s, CH$_2$OH) and 6.8 ppm (m, aryl protons) of the formula:

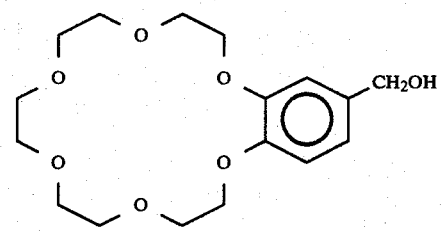

The method of Example I is followed to produce the methacrylic ester of 4-methylolbenzo-18-crown-6-ether and polymerization of the resultant 4-methylolbenzo-18-crown-6 methacrylic ester is likewise effected utilizing the method of Example I.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

I claim:

1. An acrylic ester polymer comprised of a moiety having the formula:

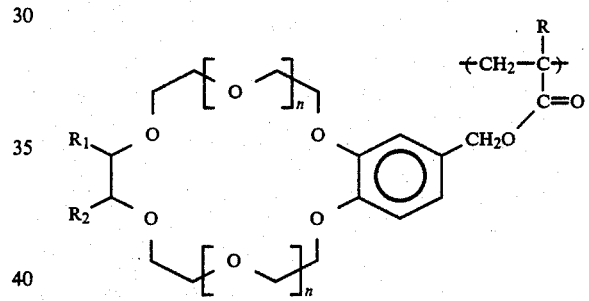

wherein the acrylic ester bearing phenyl ring denoted in the formula is unsubstituted or alkyl substituted, said alkyl substituents containing from 1 to 4 carbon atoms; and, wherein n=1–3, R is hydrogen or methyl and R$_1$ and R$_2$ are independently hydrogen or R$_1$ and R$_2$ together are: (1) an unsubstituted phenyl ring formed by R$_1$ and R$_2$ in combination with the macrocyclic ether ring or (2) an alkyl substituted phenyl ring wherein the alkyl substituents contain from 1 to 4 carbon atoms, said alkyl substituted phenyl ring formed by R$_1$ and R$_2$ in combination with the macrocyclic ether ring.

2. The acrylic ester polymer of claim 1 wherein n is 1.
3. The acrylic ester polymer of claim 1 wherein n is 2.
4. The acrylic ester polymer of claim 1 wherein R is hydrogen.
5. The acrylic ester polymer of claim 1 wherein R is methyl.
6. The acrylic ester polymer of claim 1 wherein R$_1$ and R$_2$ together are a phenyl ring.

* * * * *